(12) United States Patent
Ouchi

(10) Patent No.: US 6,224,555 B1
(45) Date of Patent: May 1, 2001

(54) ULTRASONIC DETECTOR INSERTABLE INTO BODY CAVITY

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/327,463

(22) Filed: Jun. 8, 1999

(30) Foreign Application Priority Data

Jun. 12, 1998 (JP) .................................................. 10-164650

(51) Int. Cl.⁷ .......................................................... A61B 8/00
(52) U.S. Cl. ............................................................. 600/439
(58) Field of Search ............................... 600/459, 437, 600/439, 461, 471; 604/197, 198; 606/185

(56) References Cited

U.S. PATENT DOCUMENTS

| | | | |
|---|---|---|---|
| 4,763,662 | * | 8/1988 | Yokoi ..................... 600/437 |
| 5,398,690 | * | 3/1995 | Batten et al. ............ 600/461 |
| 5,499,630 | | 3/1996 | Hiki et al. . |
| 5,601,588 | * | 2/1997 | Tonomura et al. ...... 606/185 |
| 5,873,828 | * | 2/1999 | Fujio et al. .............. 600/439 |
| 5,931,787 | * | 8/1999 | Dietz et al. ............. 600/461 |
| 6,012,867 | * | 1/2000 | Sorkin ..................... 403/288 |

FOREIGN PATENT DOCUMENTS

| | | |
|---|---|---|
| 7143985 | 6/1995 | (JP) . |
| 7184900 | 7/1995 | (JP) . |
| 7194594 | 8/1995 | (JP) . |
| 8-52138 | 2/1996 | (JP) . |
| 8126643 | 5/1996 | (JP) . |
| 8131442 | 5/1996 | (JP) . |

* cited by examiner

*Primary Examiner*—Marvin M. Lateef
*Assistant Examiner*—Ali M. Imam
(74) *Attorney, Agent, or Firm*—Greenblum & Bernstein, P.L.C.

(57) ABSTRACT

An ultrasonic detector insertable into a body cavity includes an insertion portion to be inserted into a body cavity with its tip forming part being shaped generally straight without being bent. An ultrasonic probe for lateral ultrasonic scan is provided in the front half of the tip forming part and a treatment tool projecting port is provided in the rear half of the tip forming part, directed obliquely forwardly for allowing the tip of a treatment tool (such as a puncturing needle) to project in a direction within the ultrasonic scan range. In the detector, the front half of the tip forming part is adapted to be bendable in a direction away from the ultrasonic scan range by remote handling.

10 Claims, 4 Drawing Sheets

ULTRASONIC DETECTOR INSERTABLE INTO BODY CAVITY

BACKGROUND OF THE INVENTION

The present invention relates to an ultrasonic detector insertable into a body cavity that has an ultrasonic probe and a treatment tool projecting port provided at the tip of an insertion portion to be inserted into a body cavity.

As shown in FIG. 6, an ultrasonic detector insertable into a body cavity has a tip forming part 90 provided at the tip of an insertion portion that is to be inserted into a body cavity. The tip forming part 90 has an ultrasonic probe 91 for performing an ultrasonic scan and a treatment tool projecting port 92, through which a treatment tool such as a puncturing needle projects toward an affected area. A cross section of the affected area is imaged by ultrasonic examination. In FIG. 6, a range indicated by the character "A" is the range of ultrasonic scan and the arrow "B" indicates the direction in which a treatment tool is to project.

To examine the liver, the tip of an ultrasonic detector is inserted into the stomach and a short pulse of ultrasonic waves is scanned from the probe into the liver. If it is necessary to obtain a specimen of hepatocyte tissues, a puncturing needle is pierced through the stomach wall into the liver.

For several reasons (for example, the need to provide the puncturing needle with a suitable degree of rigidity, and the practical limitations on the thickness of the insertion portion of the ultrasonic detector), it is difficult to increase the angle at which the puncturing needle projects with respect to the longitudinal axis of the tip forming part 90.

Under the circumstances, if the puncturing needle is to be pierced through the stomach wall into the liver from the illustrated ultrasonic detector, the piercing angle of the needle must be very small with respect to the stomach wall 101 (as shown in FIG. 7) and the needle cannot be pierced into the liver 102 in a precise and positive way.

To solve this problem, it has been proposed, in Unexamined Published Japanese Patent Application (Kokai) No. 143985/1995, that the tip forming part of the insertion portion is shaped to bend in a direction away from the range of ultrasonic scan, thereby ensuring that the angle at which the needle is pierced through the stomach wall is correspondingly increased.

However, if the tip forming part of the insertion portion has such a bent shape, the insertion portion will cause great pain to the patient as it is passed through the esophagus and even more pain will be felt if the insertion portion is oriented in the larynx in the "wrong direction" during removal from a body cavity.

SUMMARY OF THE INVENTION

An object, therefore, of the invention is to provide an ultrasonic detector insertable into a body cavity that permits a puncturing needle to be pierced through the stomach wall at a sufficiently large angle to ensure positive and easy puncturing, yet gives no pain to the patient when passed into and out of a body cavity.

The stated object of the invention can be attained by an ultrasonic detector insertable into a body cavity comprising an insertion portion to be inserted into a body cavity with its tip forming part being shaped generally straight without being bent. An ultrasonic probe for lateral ultrasonic scan is provided in the front half of the tip forming part, and a treatment tool projecting port is provided in the rear half of the tip forming part, directed obliquely forwardly for allowing the tip of a treatment tool (such as a puncturing needle) to project in a direction within the range of the ultrasonic scan. The front half of the tip forming part is adapted to be bendable in a direction away from said ultrasonic scan range by remote handling.

The ultrasonic detector may be provided with an urging mechanism that keeps the tip forming part in a generally straight position without being bent. If desired, the front half of the tip forming part may be bent by a manipulating wire that is pulled from the side closer to the operator. In this case, when the pulling force of the manipulating wire is removed, the front half of the tip forming part reverts to the initial state by the urging force of the urging mechanism.

The present disclosure relates to the subject matter contained in Japanese patent application No. Hei. 10-164650 (filed on Jun. 12, 1999), which is expressly incorporated herein by reference in its entirety.

DESCRIPTION OF THE PREFERRED EMBODIMENT

An embodiment of the invention is described below with reference to accompanying drawings.

Figure 1:
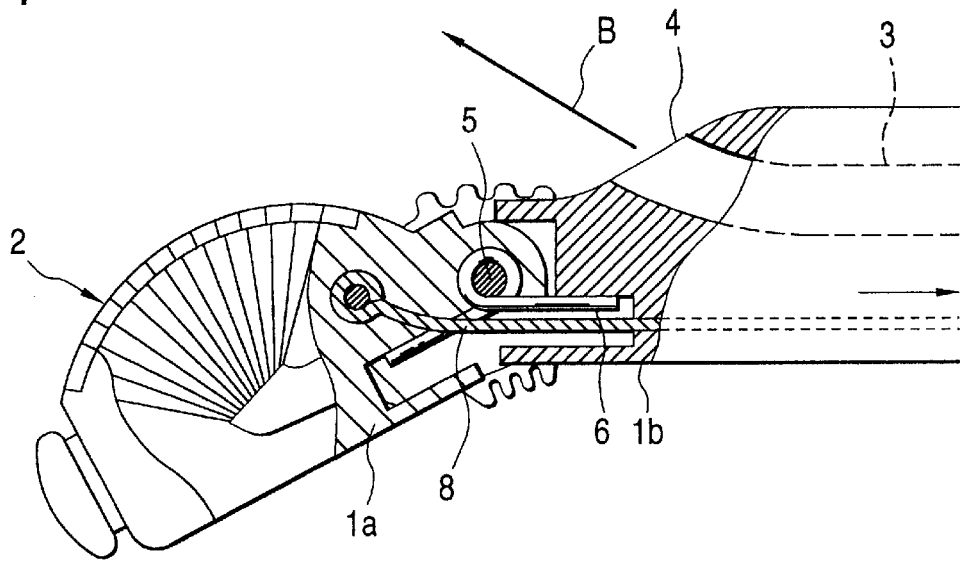
FIG. 1 is a partial side sectional view of an ultrasonic detector, with its tip bent, of a type that is insertable into a body cavity according to an embodiment of the present invention.
Figure 2:
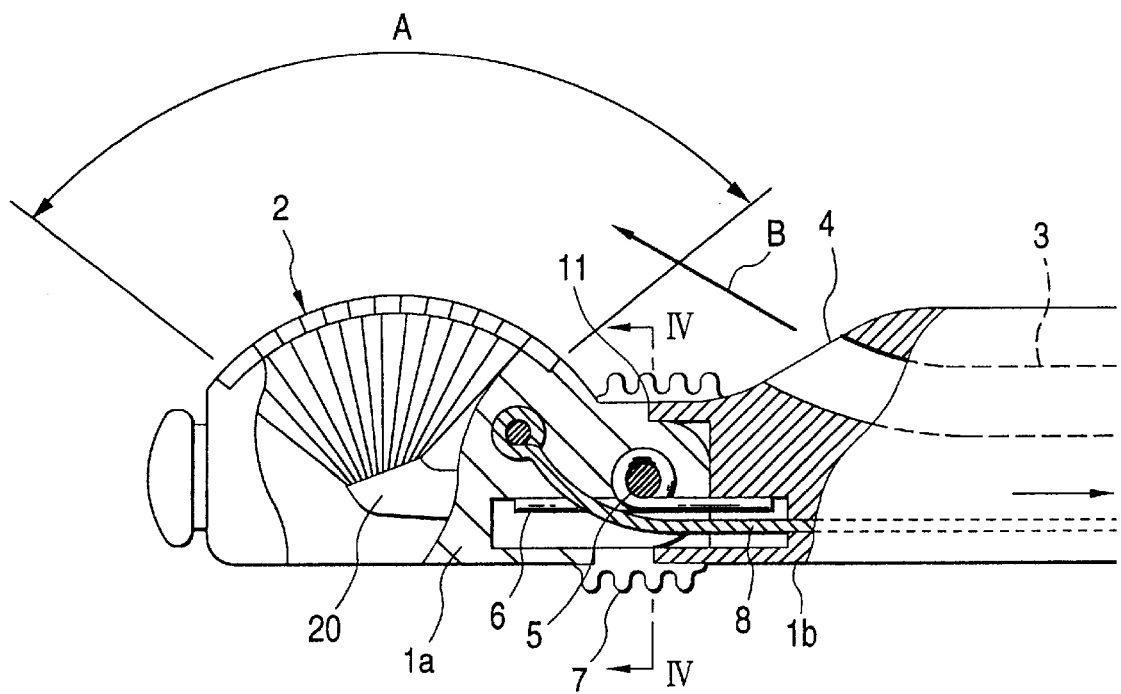
FIG. 2 is a partial side sectional view of the same ultrasonic detector, with its tip held straight.

FIG. 2 shows the tip of the insertion portion of an ultrasonic detector of a type that can be inserted into a body cavity. The tip forming part is to be coupled to the tip of a flexible tube FT in FIG. 5 that is to be inserted into a body cavity. As illustrated, the tip forming part is made up of a front half 1a and a rear half 1b that are coupled to each other with a coupling shaft 5 such that they form a generally straight shape without being bent.

Although not shown in the drawings, a known handling section is coupled to that end of the flexible tube closer to the operator. The tip of the flexible tube (FT) is provided with a known curved portion that can be bent in any direction at any angle by remote handling of the handling section.

The front half 1a of the tip forming part is provided with an ultrasonic probe 2 for lateral ultrasonic scan through a range A. The ultrasonic probe 2 may be operable by any scanning method. A signal cable 20 is connected to the ultrasonic probe 2.

The rear half 1b of the tip forming part is provided with a treatment tool projecting port 4 from which the tip of a treatment tool (such as a puncturing needle) that is to be passed into or out of a treatment tool insertion channel 3 projects. The port 4 is directed obliquely forwardly such that the tip of a treatment tool projects toward a direction within the range of ultrasonic scan A. An arrow "B" indicates the direction at which the treatment tool projects.

It should be noted that if the angle the projecting treatment tool forms with the longitudinal axis of the rear half 1b of the tip forming part is unduly great, the resistance to the passage of the treatment tool increases making it difficult to pass the treatment tool into or out of the channel 3; hence, the angle of projection should typically be restricted to the range of from about 10 to about 20 degrees. The rear half 1b of the tip forming part has built-in optics (not shown) to enable optical observation of the interior of a body cavity.

The front half 1a and the rear half 1b of the tip forming part are rotatably coupled with the coupling shaft 5 so that the front half 1a can be bent in a direction away from the ultrasonic scan range A. The joint is provided with an elastic, rubber-made, bellows-like jacket 7 to ensure watertightness.

Figure 3:
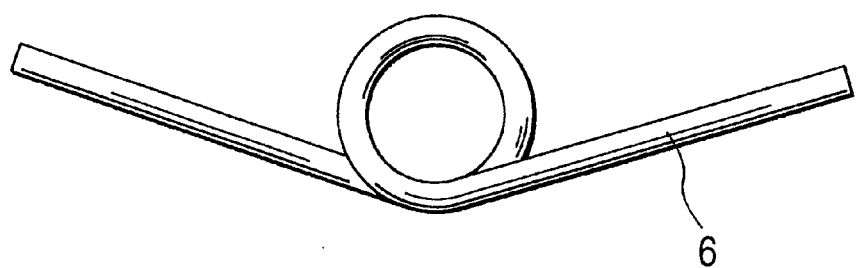
FIG. 3 is a side view of a spring loaded in the same ultrasonic detector.

The front half 1a and the rear half 1b of the tip forming part are loaded with a spring 6 which is shown individually in FIG. 3 and which urges them in the direction of rotation about the coupling shaft 5. Due to the urging force of the spring 6, the stopper 11 of the rear half 1b normally contacts the mating surface of the front half 1a to keep the tip forming part in a straight position.

Figure 4:
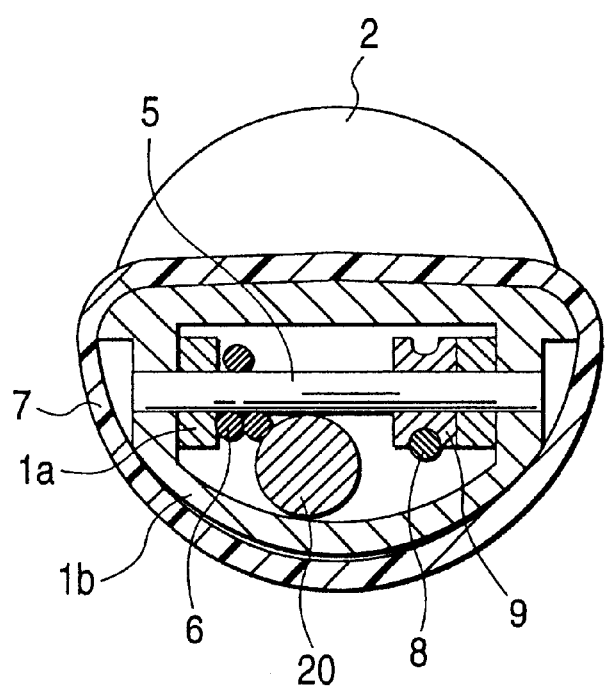
FIG. 4 is section IV—IV of FIG. 2.

The front half 1a of the tip forming part engages the tip of a manipulating wire 8 that is pulled from the handling section (not shown). As is clear from FIG. 4, which shows section IV—IV of FIG. 2, a pulley 9 is fitted rotatably around the coupling shaft 5 and the manipulating wire 8 is guided along the pulley 9 to pass on the back side of the tip forming part.

Due to this arrangement, if the manipulating wire 8 is pulled from the handling section, the front half 1a of the tip forming part turns about the coupling shaft 5 to bend in a direction away from the ultrasonic scan range A. If the pulling force of the maneuvering wire 8 is removed, the urging force of the spring 6 brings the front half 1a back to the initial state where the front half 1a aligns linearly with the rear half 1b.

To examine the liver, the ultrasonic detector having the construction described above is inserted into the stomach. After examination, the detector is removed from the stomach. In both processes, the tip forming part of the detector is kept straight so that there will be no problem during the passage through the esophagus and the larynx.

If a puncturing needle is to be pierced through the stomach wall into the liver, the front half 1a of the tip forming part is brought into intimate contact with the stomach wall 101 (see FIG. 5) in such a way that ultrasonic scan of the liver 102 is possible; thereafter, the manipulating wire 8 is pulled.

Then, the tip forming part bends in the joint between the front half 1a and the rear half 1b and the projecting direction B of the needle forms a sufficiently large angle (say, 30 to 60°) with the surface of the stomach wall 101 that the needle can be easily pierced through the stomach wall 101 and enter the liver 102 in a precise and positive way.

Figure 5:
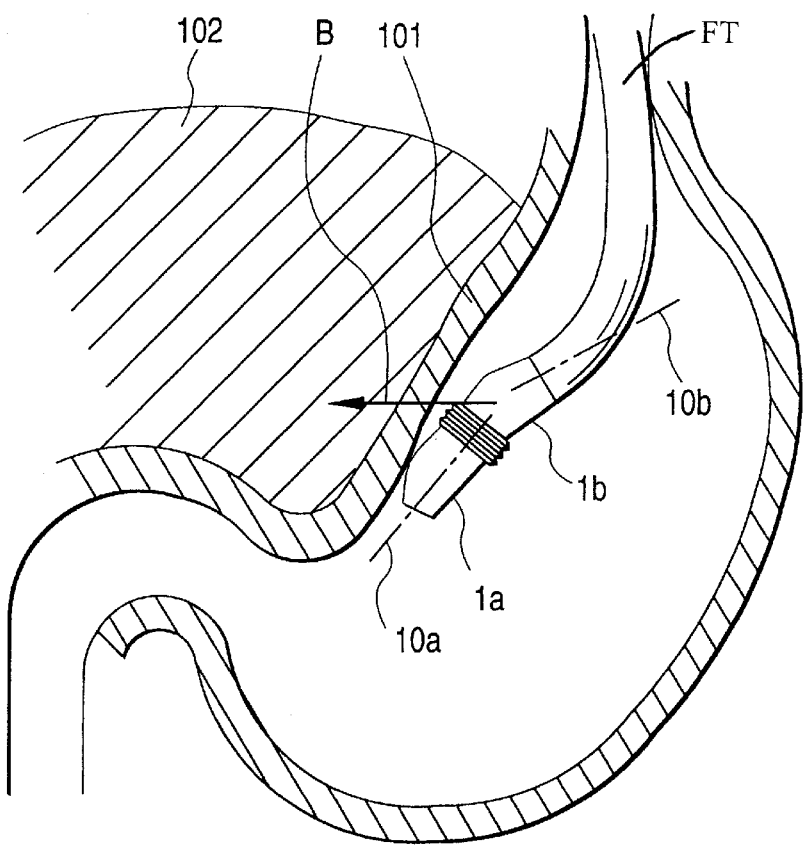
FIG. 5 is a sketch showing how the same ultrasonic detector is used in practice.
Figure 6:
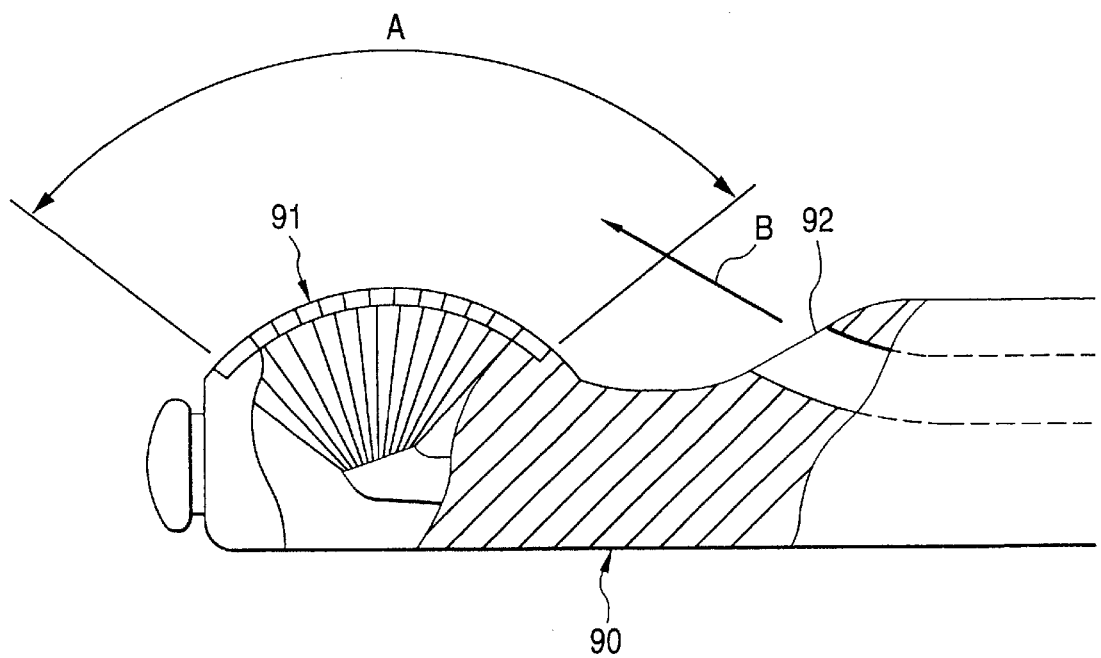
FIG. 6 is a partial side sectional view of the tip portion of a related ultrasonic detector of a type that can be inserted into a body cavity.
Figure 7:
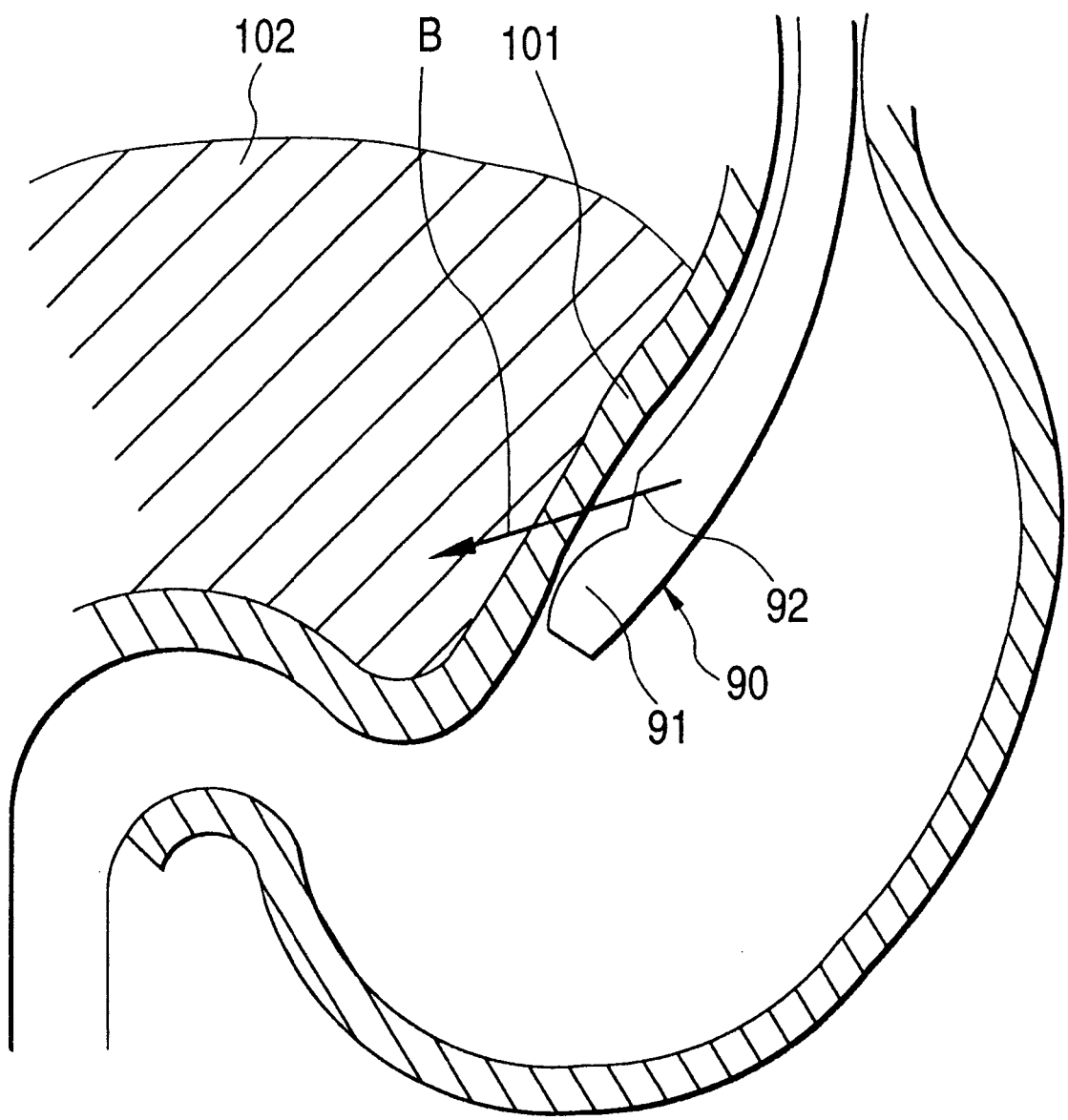
FIG. 7 is a sketch showing how the related ultrasonic detector is used in practice.

As shown in FIG. 5, the projecting direction (arrow "B") of the puncturing needle remains at an unstrained small angle as in the related art with respect to the longitudinal axis 10b of the rear half 1b of the tip forming part. However, in the present invention, the projecting direction can be adjusted to have a great angle with respect to the longitudinal axis 10a of the front half 1a (which comes in intimate contact with the stomach wall 101).

It should be noted that with an ultrasonic detector of the type contemplated by the invention, i.e., insertable into a body cavity, the angle through which the front half 1a of the tip forming part bends with respect to the rear half 1b is optionally about 15 to 45°. However, if necessary, the bending angle may be greater than 45°.

The applicability of the ultrasonic detector of the invention is, by no means, limited to the liver. The ultrasonic detector of the invention is also useful in the case where a puncturing needle is to be pierced into other organs (such as the spleen).

According to the present invention, the front half of the tip forming part of an ultrasonic detector is bent in a direction away from the range of ultrasonic scan. This allows the projecting direction of a puncturing needle to remain at an unstrained small angle with respect to the longitudinal axis of the rear half of the tip forming part, while the projecting direction can be adjusted to have a great angle with respect to the longitudinal axis of the front half. As a result, the needle can be pierced through the stomach wall at a sufficiently large angle to enter the liver or other organ in an easy and yet positive manner. As a further advantage, the insertion portion of the detector can be passed into or out of a body cavity in an easy and safe manner, i.e., with the tip forming part kept in a straight position that gives no pain to the patient.

What is claimed is:

1. An ultrasonic detector insertable into a body cavity, the detector comprising:

an insertion portion to be inserted into a body cavity, a tip forming part of said insertion portion being generally straight;

an ultrasonic probe for lateral ultrasonic scan provided in a front portion of said tip forming part;

a treatment tool projecting port provided in a rear portion of said tip forming part and that extends parallel to a rear longitudinal axis of a rear portion of said tip forming part toward a front portion of said tip forming part and is angled with respect to said longitudinal axis before a front portion of said tip forming part, directing a treatment tool inserted in said port to be angled with respect to said rear portion of said tip forming part, allowing the tip of the treatment tool to project in a direction within the range of said lateral ultrasonic scan, wherein the front portion of said tip forming part is inclinable relative to the rear portion of said tip forming part and away from the treatment tool inserted in said port by remote handling.

2. The ultrasonic detector according to claim 1, further comprising:

an urging mechanism that biases said front half and said rear half of said tip forming part toward a generally straight position.

3. The ultrasonic detector according to claim 2, wherein the front half of said tip forming part is bent by a manipulating wire that is pulled from the side of the insertion portion closer to the operator and, when a pulling force of said maneuvering wire is removed, reverts to an initial state by an urging force of said urging mechanism.

4. The detector according to claim 1, said treatment tool projecting port being oriented in a projecting direction, wherein an angle between said second longitudinal axis and the projecting direction is variable.

5. The detector according to claim 1, wherein said second tip forming part is pivotably coupled to said first tip forming part via a coupling shaft.

6. The detector according to claim 1, wherein said first and second tip forming part are biased relative to one another by a spring.

7. The detector according to claim 1, further comprising:

a stopper provided on the first tip forming part, said stopper being in contact with a mating surface provided on said second tip forming part when said second longitudinal axis is aligned with said first longitudinal axis.

8. The detector according to claim 1, wherein a manipulating wire is connected to said second tip forming part to move said second tip forming part relative to said first tip forming part.

9. An ultrasonic detector having a flexible tube insertable into a body cavity, said detector comprising:

a first tip forming part connected to said flexible tube, said first tip forming part having a first longitudinal axis and a treatment tool projecting port oriented at a fixed angle with respect to said first longitudinal axis; and a second tip forming part location on an opposite side of said first tip forming part with respect to said flexible tube, and movably coupled to said first tip forming part, said second tip forming part having a second longitudinal axis inclinable relative to the first tip forming part and away from a treatment tool inserted in said port and an ultrasonic probe.

10. The detector according to claim 9, wherein said second tip forming part is movable relative to said first tip forming part to make said second longitudinal axis in align with said first longitudinal axis.

* * * * *